(12) United States Patent
Jadwizak et al.

(10) Patent No.: US 9,776,011 B2
(45) Date of Patent: Oct. 3, 2017

(54) IMPLANTABLE CURVED SHAPING PART FOR EXTERNALLY SHAPING AN IMPLANTABLE ELECTRODE LINE OR A CATHETER

(71) Applicant: BIOTRONIK SE & Co. KG, Berlin (DE)

(72) Inventors: Detmar Jadwizak, Erkner (DE); Carsten Fruendt, Berlin (DE); Dajana Kaiser, Berlin (DE); Gordon Hillebrand, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 15/090,835

(22) Filed: Apr. 5, 2016

(65) Prior Publication Data

US 2016/0303382 A1 Oct. 20, 2016

Related U.S. Application Data

(60) Provisional application No. 62/149,675, filed on Apr. 20, 2015.

(51) Int. Cl.
*A61N 1/375* (2006.01)
*A61N 1/05* (2006.01)
*A61M 25/00* (2006.01)

(52) U.S. Cl.
CPC ............ *A61N 1/375* (2013.01); *A61N 1/056* (2013.01); *A61N 2001/0585* (2013.01)

(58) Field of Classification Search
None
See application file for complete search history.

(56) References Cited

U.S. PATENT DOCUMENTS

| 5,925,073 | A | 7/1999 | Chastain et al. |
| 6,556,873 | B1 | 4/2003 | Smits |
| 8,086,317 | B2 * | 12/2011 | Finch ............... A61N 1/36017 607/117 |
| 8,954,162 | B2 * | 2/2015 | Bonde ............... A61B 17/3468 607/1 |
| 2005/0004565 | A1 * | 1/2005 | Vanney ............. A61B 18/1492 606/41 |
| 2007/0293923 | A1 | 12/2007 | Soltis et al. |

(Continued)

FOREIGN PATENT DOCUMENTS

| EP | 2 024 014 B1 | 11/2013 |
| WO | 2006116595 | 11/2006 |

OTHER PUBLICATIONS

European Search Report and Annex to the European Search Report on European Patent Application No. EP 16 16 1307, dated Jun. 1, 2016 (6 pages).

*Primary Examiner* — Brian T Gedeon
(74) *Attorney, Agent, or Firm* — Buchanan Ingersoll & Rooney PC

(57) ABSTRACT

An implantable curved shaping part for externally shaping an implantable electrode line or a catheter, wherein the shaping part has a continuous first lumen to allow a portion of the electrode line or of the catheter to pass through, wherein the shaping part is formed as an injection molded part or has at least one injection molded portion, and an elongated, rigid yet flexible bend impression element is fixed within the wall or to the inner wall.

13 Claims, 7 Drawing Sheets

(56) References Cited

U.S. PATENT DOCUMENTS

| | | | |
|---|---|---|---|
| 2008/0147013 A1* | 6/2008 | Breton | A61M 25/0105 604/174 |
| 2010/0114114 A1* | 5/2010 | Tockman | A61M 25/0147 606/129 |
| 2010/0198208 A1* | 8/2010 | Napp | A61B 1/00078 606/27 |
| 2016/0151608 A1* | 6/2016 | Aklog | A61M 25/04 604/506 |

* cited by examiner

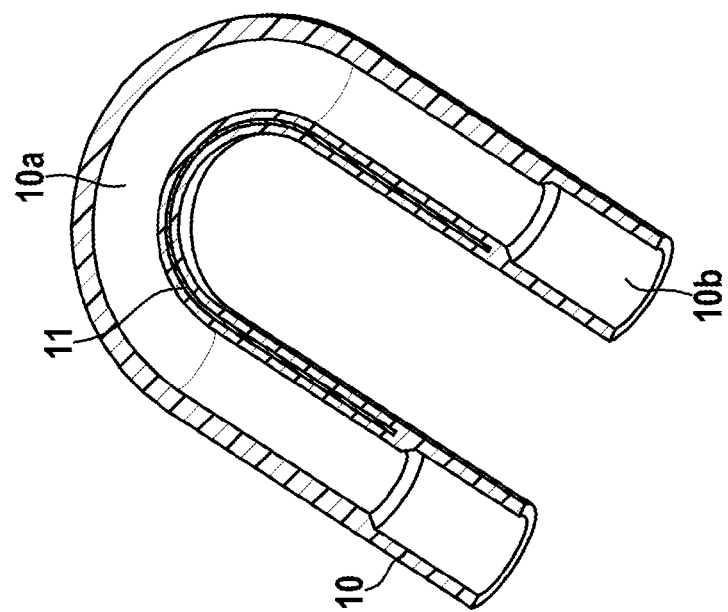
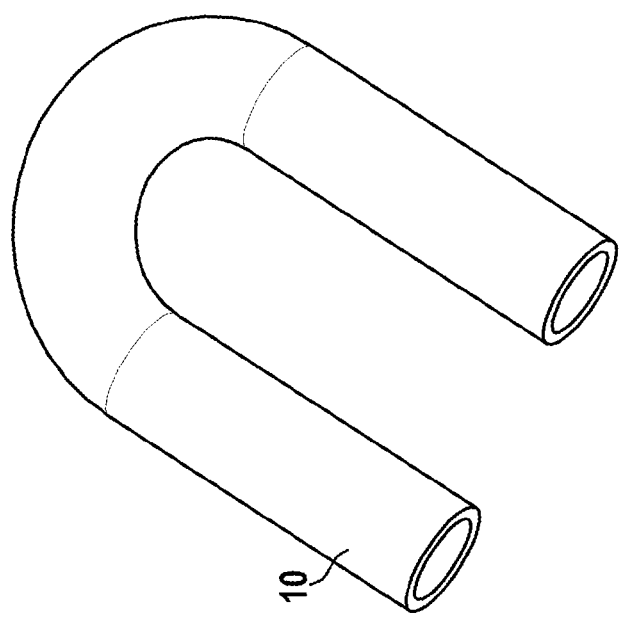
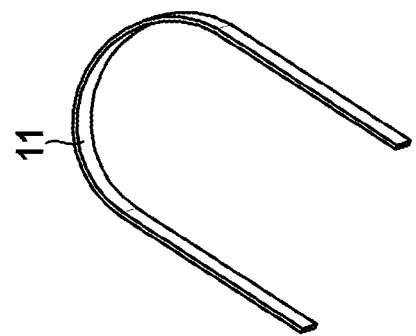

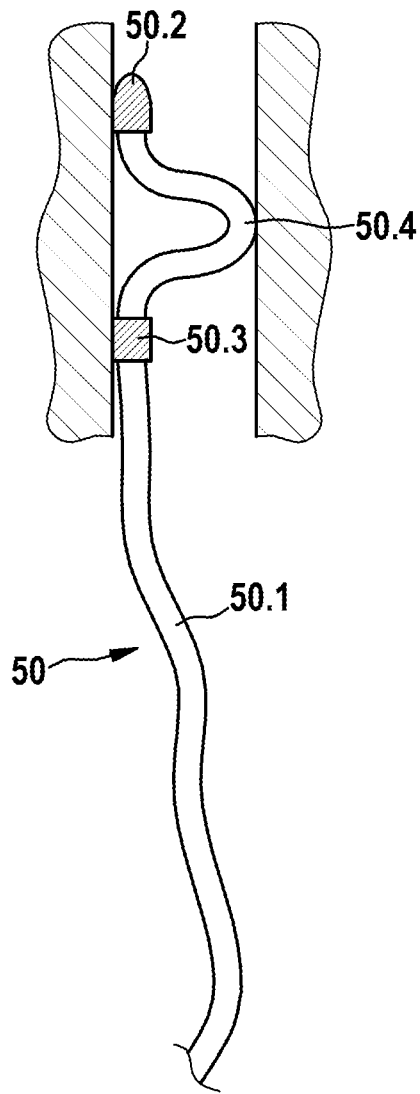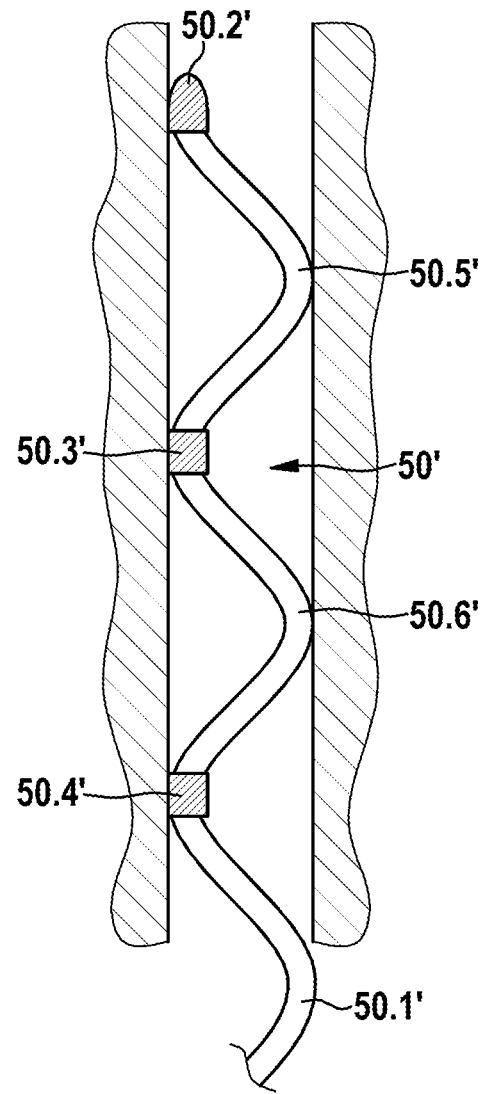
FIG. 5A
FIG. 5B

IMPLANTABLE CURVED SHAPING PART FOR EXTERNALLY SHAPING AN IMPLANTABLE ELECTRODE LINE OR A CATHETER

CROSS-REFERENCE TO RELATED APPLICATIONS

This patent application claims the benefit of U.S. Provisional Patent Application No. 62/149,675, filed on Apr. 20, 2015, which is hereby incorporated by reference in its entirety.

TECHNICAL FIELD

The present invention relates to an implantable curved shaping part for externally shaping an implantable electrode line or a catheter, wherein the shaping part has a continuous first lumen to allow a portion of the electrode line or of the catheter to pass through. The present invention also relates to an electrode line arrangement or catheter arrangement that is formed with at least one such shaping part.

BACKGROUND

Implanted medical electrode lines (also referred to as "electrodes" for short) have to be positioned in the body of the patient at a suitable point and also fixed sufficiently durably in this position in order to attain the desired therapeutic effects reliably and durably. A multitude of different developments for solving this problem have therefore been provided since the introduction of the first implantable cardiac pacemaker.

In order to fix electrode lines in vessel portions or relatively narrow hollow organs in a precisely positioned manner, electrode lines with impressed curvatures in the distal end region have already been proposed for some time, which, following the implantation and the removal of the guide wire or the stylet, tense up to a certain extent between opposite walls of the vessel or hollow organ on account of the curved profile of said electrode lines. A rather reliable position fixing that is also stable in the long term can thus be achieved. An example of such a construction is described in U.S. Pat. No. 5,925,073.

In this context electrode lines having special inner structures have also been developed, with which a rigidity or flexibility that is variable over the longitudinal extent is to be provided; in this regard see U.S. Pat. No. 6,556,873 or European Patent No. 2 024 014 B1, for example.

Special "CRT electrodes" are implanted in coronary sinus vessels in the region of the left ventricle. To this end, these electrodes have a "passive" fixing of the above-mentioned type, the distal region of the electrode being provided with one or more curvatures. During implantation this curvature is put straight by an internally arranged stylet. If this stylet is withdrawn, the electrode returning into the curved state exerts force onto the vessel inner wall and, thus, anchors the electrode at the desired location thereof.

From a technical viewpoint the following possible implementations of such a solution are known and used:

1. Production of an electrode curvature by annealing an MP35N coil arranged in the line body.
2. Production of an electrode curvature by mechanical deformation (cold forming) of a coil arranged in the line body. This is preferably applied in the case of coradial coils, since here each individual wire has an insulation layer of which the melting point is below the annealing temperature of the coil and, therefore, an annealing process cannot be applied.
3. Production of an electrode curvature by thermal deformation of plastic insulation tubes.
4. Production of an electrode curvature by a silicone part injection molded in a curved mold.
5. Production of an electrode curvature by a silicone injection molded part with tension band.

All of these solutions have certain disadvantages, of which the following are specified here:

Firstly: With use of an ETFE-coated coradial coil, an annealing method cannot be applied. However, in order to form a plurality of poles in a small diameter, the use of such a coradial coil is necessary.

Secondly: The desired angle of curvature and the desired force of curvature are not produced by a mechanical deformation of the coil alone.

Thirdly: With use of silicone it is not possible to provide any subsequent thermal deformation. Silicone is an end-cross-linked material, which can no longer deform after the vulcanizing process. The use of silicone in the distal region of a CRT electrode is of great advantage, since flexibility and fatigue strength of a plastic material are superior for this application.

Fourthly: A silicone injection molded part that is injected in a curved shape does not produce the desired angle of curvature and the descried force of curvature (return force).

Fifthly: Due to the small diameter of an electrode line, only very small wall thicknesses are available for a tension band. Furthermore, a silicone injection molded part with tension band can be produced only in a complicated and complex production method with relatively high error potential.

The present invention is directed toward overcoming one or more of the above-mentioned problems.

SUMMARY

An object of the present invention is therefore to provide an improved solution for producing an electrode line (or also a catheter) that can be fixed passively in a vessel or relatively narrow hollow organ and that functions in particularly reliably and durably, can be easily handled during the implantation, and is also acceptable from cost aspects.

According to the fundamental considerations of the inventors, a silicone part is to be developed that, with a smaller diameter, low wall thickness, short length and simple production method, performs the function of curving a coradial coil and, thus, fixing the electrode in a vessel or hollow organ (especially in the coronary vessel). This silicone part must be flexible, be capable of being put straight, and must be durable and must also have the greatest possible return force.

At least the above object is achieved by an implantable curved shaping part having the features of claim 1. Expedient developments of the inventive concept are specified in the dependent claims. Furthermore, an electrode line arrangement having the features of claim 11 and a catheter arrangement having the features of claim 14 are provided.

In view of the extremely advantageous properties of soft silicone, these properties being inadequate, however, from some aspects, the present invention includes the concept of integration into the silicone part of an element intensifying the shaping force of the element on the electrode or catheter line received therein. This will be referred to hereinafter synonymously as a "bend impression element" or "force-intensifying element". It is fixed within the wall or to the inner wall of the shaping part, which is formed as an injection molded part or has at least one injection molded portion.

In one embodiment of the present invention, the shaping part is formed as a part that is U-shaped or V-shaped in the use state with a rounded tip. The use state is understood to be the state with electrode line or catheter line or stiffening guide wire or stylet received in the shaping part. Depending on the length of the shaping part, the natural basic shape thereof (without electrode line or catheter line) may absolutely comprise a segment of a circle of more than 180°, and may even have in portions a coil or helix form. The ends of the shaping part are preferably substantially elongated.

In a further embodiment, the injection molded part is formed as a silicone part with low Shore hardness, in particular of 50 Shore or less. It is a key advantage of the present invention that, due to the use of the "force-intensifying element", such a soft silicone material, which is advantageous from many viewpoints, can be used. However, silicone masses with higher Shore hardnesses could generally also be used (for example, up to 80 Shore).

In a further embodiment, the first lumen has a widened diameter at both ends, such that space is created for an inner adhesive layer. For practical use of the electrode line or catheter arrangements in question, a fixed integral bond between the shaping part and a predetermined portion of the electrode line or catheter line (in particular, bordering an electrode pole) is to be created already from a licensing viewpoint. In order to achieve this without outer diameter enlargement (which would therefore be obstructive during use), space for an (in particular, annular) adhesive layer is to be created on the inner wall of the shaping part.

In further embodiments of the present invention, the shaping part is formed as an extruded silicone tube with overmolded ends, which determine the widened cross section of the first lumen. This silicone tube has at least one second lumen, in which the bend impression element is arranged. The second lumen is, in particular, continuous over the total length of the shaping part; alternatively, however, it is also possible to provide a second lumen that is open only from one end. In any case the extent of the second lumen is to be selected such that the bend impression end or force-intensifying function can be attained sufficiently. In the normal case, the second lumen should thus extend in any case over the much larger part of the length of the shaping part.

In further embodiments of the present invention, the bend impression element is a resiliently rigid curved plastic rod. The rigidity and spring effect or elasticity properties of the rod are to be coordinated with the mechanical properties of a guide wire or stylet used in the specific application in the implantation process, such that the shaping part matches the profile of the guide wire or stylet to the greatest possible extent. At the same time, the properties of the electrode line (without guide wire or stylet) are to be taken into consideration such that the bend impression element is "stronger" than the electrode line or catheter line, i.e., can provide said line with the desired curvature resiliently.

In a special variant of the mentioned embodiment, the bend impression element may be a plastic rod or strip made of a memory material. In this embodiment, a coordination of the mechanical properties between electrode line body, guide wire or stylet and shaping part is not as important as mentioned above, because the force-intensifying or bend impression effect of the rod is only produced once said rod has transferred into the memory form.

In a further embodiment, the bend impression element is a biased plastic rod or strip provided with a curvature by annealing. For such a plastic rod or strip, the boundary conditions explained further above in relation to the rigidity and elasticity of said rod apply to a large extent.

In further embodiments, the shaping part comprises a plurality of bend impression elements, which, in particular, are each arranged in a pre-formed second lumen. In view of the increased development and production outlay, such embodiments do not appear to be preferred from the present viewpoint, but could provide advantages in order to attain special curvature profiles and/or a predetermined behavior during the implantation process.

In accordance with one embodiment of the proposed electrode line arrangement, the shaping part completely surrounds a portion between two electrode poles, in such a way that a first end of the shaping part directly contacts a first electrode pole and a second end of the shaping part directly contacts a second electrode pole. The requirements mentioned further above with regard to the ongoing reliability, especially for mechanical protection, for insulation and tensile force transmission, which are also expressed in licensing requirements, are hereby taken into consideration.

In further embodiments of the electrode line arrangement, two or more U-shaped or V-shaped shaping parts are arranged in succession in the longitudinal direction on the electrode line with oppositely directed curvature, such that a distal end portion of the electrode line on the whole has impressed a substantially S-shaped, Z-shaped, J-shaped, undulating or zigzagged profile.

Further embodiments, features, aspects, objects, advantages, and possible applications of the present invention could be learned from the following description, in combination with the Figures, and the appended claims.

DESCRIPTION OF THE DRAWINGS

Advantages and expedient features of the invention will also emerge from the following description of exemplary embodiments with reference to the Figures, in which:

FIGS. 1A-1C show perspective illustrations and a perspective sectional view of a first exemplary embodiment of the present invention.

FIGS. 5A-5B show perspective illustrations of two embodiments of an electrode line arrangement according to the present invention.

DETAILED DESCRIPTION

FIGS. 1B-1C show a shaping part 10 in accordance with a first exemplary embodiment of the present invention, and FIG. 1A shows a U-shaped rigid-resilient plastic part 11, for example, with circular or rectangular cross section, which is integrated as a bend impression element in the shaping part 10.

The shaping part 10 is produced by overmolding the U-shaped plastic part 11 with a soft silicone in a suitable injection mold. During the overmolding, the end portions 10b with widened inner diameter and also the central lumen 10a are produced at the same time. Inner and outer lateral layers of the shaping part 10 are thus produced in one injection molding process.

Figure 2C:
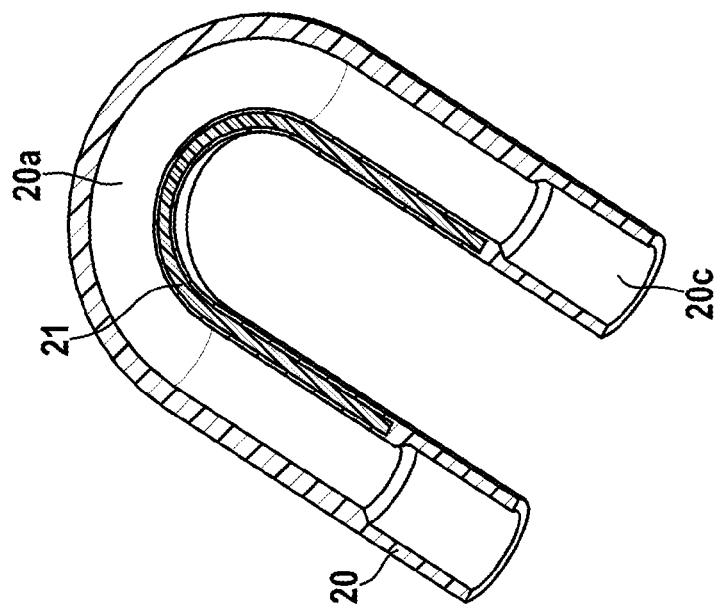
FIGS. 2A-2C show perspective illustrations and a perspective sectional view of a second exemplary embodiment of the present invention.
Figure 2B:
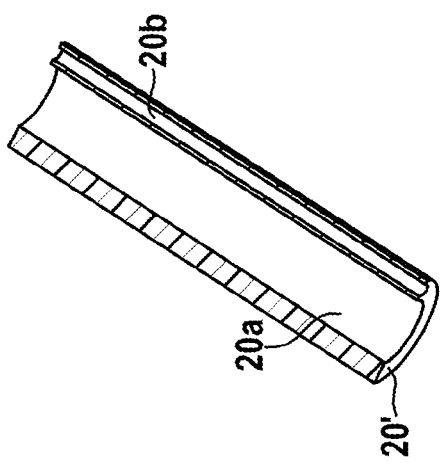
Figure 2A:
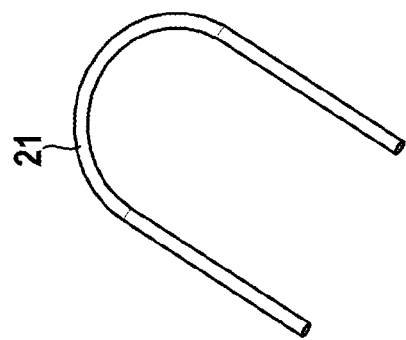

FIG. 2C shows, as further exemplary embodiment, a second shaping part 20, and FIG. 2B shows, as associated preliminary product or semi-finished product, an extruded silicone tube 20' having a central first lumen 20a and a second lumen 20b, which is arranged in the wall and has a much smaller diameter. FIG. 2A shows a rigid-resilient plastic rod 21 with circular or rectangular cross section, which is introduced into the second lumen 20b of the silicone tube 20' of circular or semi-circular cross section and provides this, as bend impression element, on the whole with a U-shape. As can be seen in FIG. 2C, the shaping part 20 is lengthened at the ends by overmolding of the extruded plastic tube, wherein widened end portions 20c of the central lumen 20a are again formed.

In its outer form, the shaping part 20 according to FIG. 2C is, fundamentally, no different from the shaping part 10 according to FIGS. 1B-1C; the main difference lies in that fact that, in the case of the second shaping part 20, the bend impression element is introduced into a second lumen of the original silicone tube, said lumen being continuous lengthwise, whereas the first shaping part 10 is placed in the injection mold and is only embedded in the wall of the part during the subsequent overmolding.

Figure 3A:
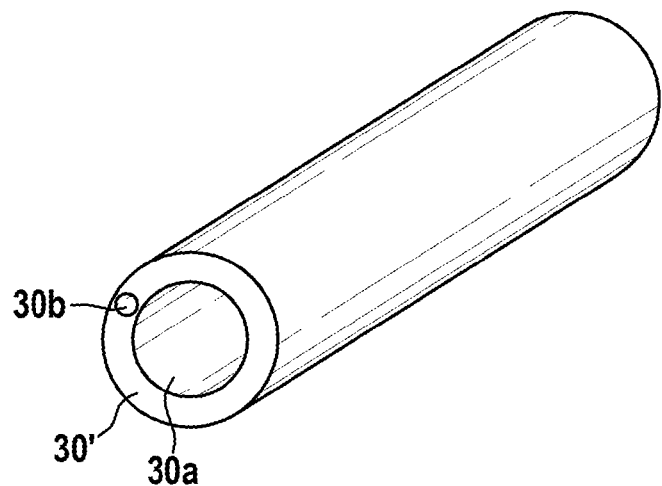
FIGS. 3A-3E show perspective illustrations and a perspective sectional view of a third exemplary embodiment of the present invention.
Figure 3B:
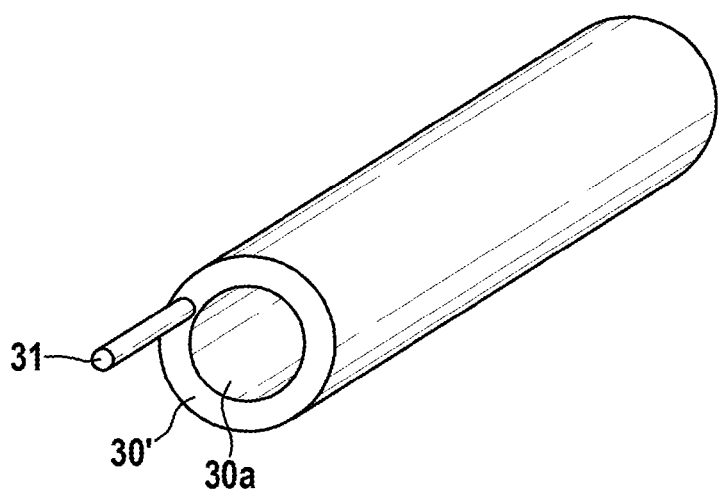
Figure 3C:
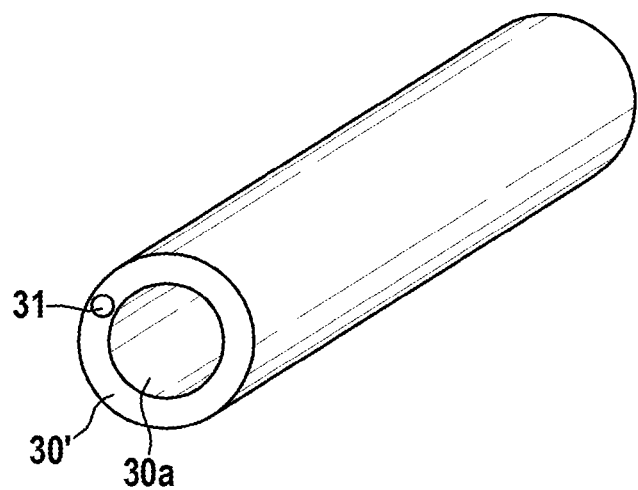
Figure 3D:
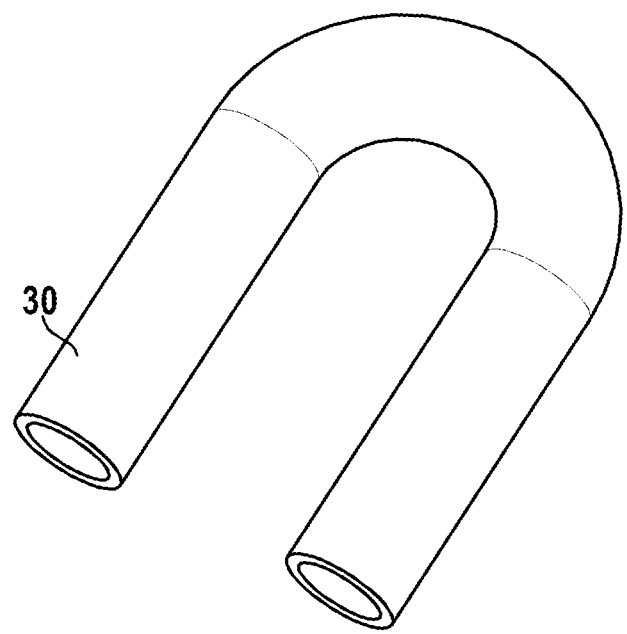
Figure 3E:
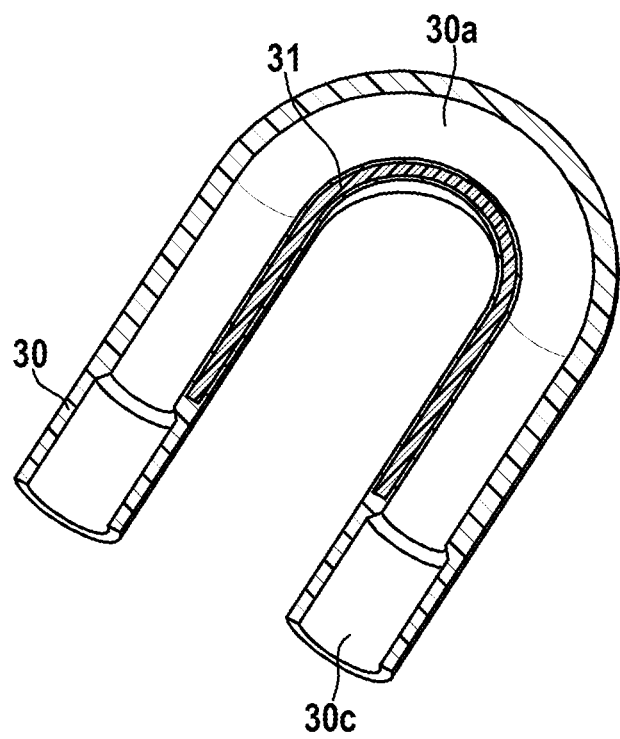
Figure 4A:
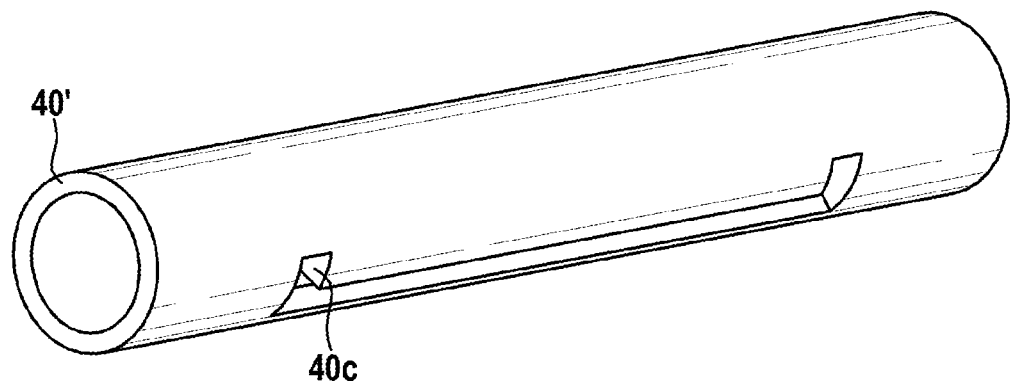
FIGS. 4A-4D show perspective illustrations and longitudinal sectional illustrations of a fourth exemplary embodiment of the present invention.
Figure 4B:
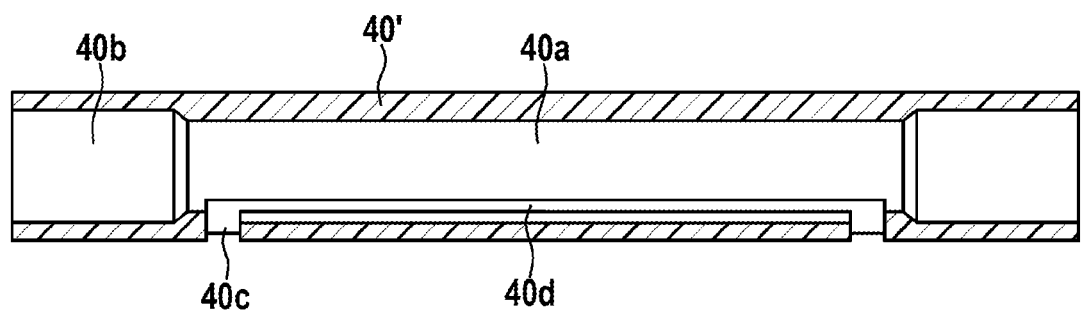
Figure 4C:
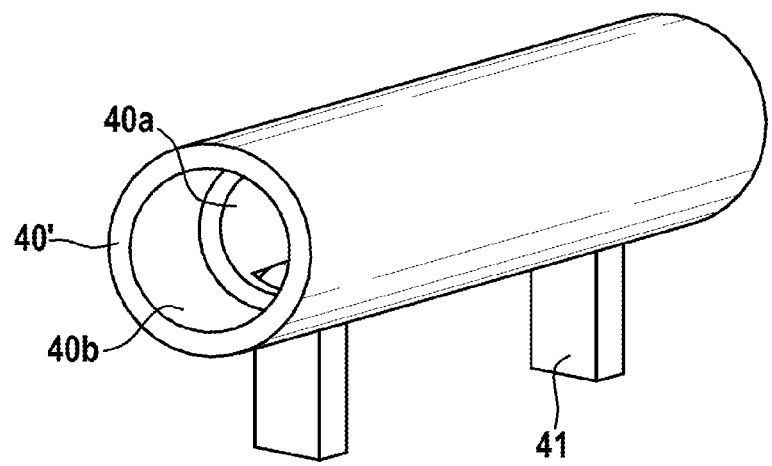
Figure 4D:
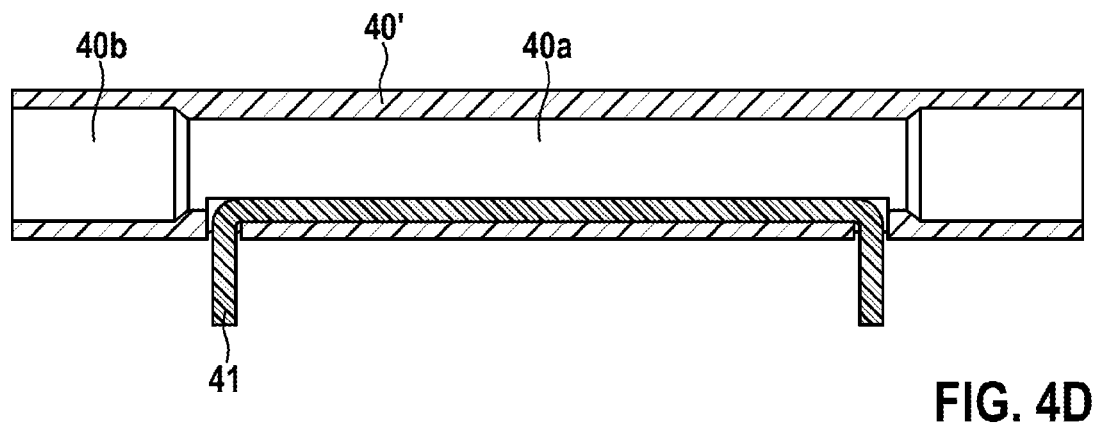

The shaping pat 30 according to a third exemplary embodiment shown in FIGS. 3D-3E is also structured similarly in essence, the preliminary product 30' of said shaping part stretched in a straight line being illustrated in FIGS. 3A-3C. Here too, a silicone tube with a central lumen 30A of large diameter and a second lumen 30b, which is arranged in the wall and has a much smaller diameter, is used as preliminary product. As shown in FIGS. 3B-3C, a plastic strip 31, that in its initial form is also stretched in a straight line, is introduced into the second lumen 30b and is anchored once tensioned. Here, a semi-circular lumen with a plastic strip (rectangular cross section) can also be used.

During a subsequent annealing of the silicone tube, the plastic strip 31 fixed at both ends of the preliminary product 30' contracts in such a way that it entrains the entire tube into a U-shape. In this state, the silicone tube is then provided with ends with widening portions 30c of the central lumen 30a, again by injection molding. As mentioned with the aforementioned embodiments, an additional silicone casing layer can also be placed over the entire tube. This is merely optional, however, and the ends can also contact the extruded tube bluntly.

FIGS. 4A-4D each show preliminary stages 40' of a further shaping part, which is not illustrated in the end state, but of which the end form corresponds essentially to the form of the first to third shaping part. Here, however, the shaping part is not an extruded silicone tube, as in some of the aforementioned exemplary embodiments, but is a silicone injection molded part with end portions having widened central lumen 40b, said end portions being integrally formed from the outset.

A plastic strip 41 is inserted, as a bend impression element or a force-intensifying element, via corresponding access points 40c on one side of the wall into a recess (groove) 40d intended for this purpose and running lengthwise. This bend impression element 41 is largely plastically deformable and can be transferred from the stretched state shown in FIG. 4D into a U-shape of the central portion, wherein it impresses this shape on the entire shaping part. At the same time, it has sufficient resilience in the deformed state to meet the general requirements placed on the shaping part according to the invention, as explained in greater detail above.

FIGS. 5A-5B show two configurations of electrode line arrangements that can be provided with shaping parts of the above-described type. FIG. 5A shows an electrode line arrangement 50 with an electrode line (electrode) 50.1, which has a tip electrode 50.2 and a ring electrode 50.3 as electrode poles and is deformed so as to be V-shaped in the end portion by a shaping part 50.4 shrunk-fit on the line between the two electrode poles 50.2, 50.3. The electrode line arrangement 50 thus tenses between the opposite walls of a vessel, which in turn leads in a desirable manner to the fact that the electrode poles 50.2 and 50.3 have reliable wall contact and can thus reliably performed their stimulation and/or sensing task in a durable manner.

FIG. 5B shows, as modification of this configuration, a further electrode line arrangement 50', which comprises a three-pole electrode line 50.1' with the electrode poles 50.2', 50.3' and 50.4' and two shaping parts 50.5', 50.6'. Both shaping parts are each placed between the three electrode poles around the corresponding portions of the electrode 50.1' and are tightly glued there to the electrode. It can be seen that the electrode line in this embodiment has assumed a form that is undulating on the whole in the end portion, wherein this form in turn has the desired result that all electrode poles 50.2', 50.3' and 50.4' have reliable wall contact.

The shaping parts are shrunk-fit on the electrode in a manner known per se. Shaping parts made of silicone are swollen (for example, with heptane) prior to assembly, such that the parts can be slid over the coil into the desired position—heptane escapes little by little and the silicone contracts together again and is thus shrunk fit onto the coil. If plastic reinforcement parts are integrated in this silicone part, this method can be used only to a limited extent, since plastic does not swell and the two materials may detach from one another. A further possibility is the short-term widening of the inner diameter of the shaping part by compressed air. The ends are sealed, compressed air is filled in, and the part can be mounted and placed on or over larger diameters.

In a further variant the part is mechanically widened, for example, by a number of wires of half-shells arranged internally. The part can thus also be mounted and placed here on or over larger diameters.

In addition, the present invention can also be embodied in a multitude of modifications of the examples shown here and aspects of the present invention highlighted above.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable curved shaping part for externally shaping an implantable electrode line or a catheter, wherein the shaping part has a continuous first lumen to allow a portion of the electrode line or of the catheter to pass through, wherein the shaping part is formed as an injection molded part or has at least one injection molded portion, and an elongated, rigid yet flexible bend impression element is fixed within a wall or to an inner wall of the shaping part, wherein the bend impression element is a resiliently stiff curved plastic rod or strip.

2. The shaping part according to claim 1, formed as a part that is U shaped or V shaped in the use state with rounded tip.

3. The shaping part according to claim 1, wherein the injection molded part or the injection molded portion is formed from silicone with low Shore hardness of 50 Shore or less.

4. The shaping part according to claim 1, wherein the first lumen has a widened diameter at both ends, such that space is created for an inner adhesive layer.

5. The shaping part according to claim 4, formed as an extruded silicone tube with overmolded ends, which determine the widened cross section of the first lumen, which has at least one second lumen, in which the bend impression element is arranged.

6. The shaping part according to claim 5, wherein the second lumen is continuous.

7. The shaping part according to claim 1, wherein the bend impression element is a rod made of a memory material.

8. The shaping part according to claim 1, wherein the bend impression element is a prestressed plastic rod or strip provided with a curvature by annealing.

9. The shaping part according to claim 1, having a number of bend impression elements, which are each arranged in a preformed second lumen.

10. An electrode line arrangement having an implantable electrode line and at least one shaping part according to claim 1, which surrounds a distal portion of the electrode line.

11. The electrode line arrangement according to claim 10, wherein the shaping part completely surrounds a portion between two electrode poles in such a way that a first end of the shaping part directly contacts a first electrode pole and a second end of the shaping part directly contacts a second electrode pole.

12. The electrode line arrangement according to claim 10, wherein two or more U-shaped or V-shaped shaping parts are arranged in succession in the longitudinal direction on the electrode line optionally with oppositely directed curvature, such that a distal end portion of the electrode line on the whole has a substantially S-shaped, Z-shaped, J-shaped, undulating or zigzagged profile.

13. A catheter arrangement having a catheter and at least one shaping part according to claim 1.

* * * * *